(12) United States Patent
Ueno et al.

(10) Patent No.: US 7,381,186 B2
(45) Date of Patent: Jun. 3, 2008

(54) METHOD AND APPARATUS TO ASSESS COMPARTMENT SYNDROME

(75) Inventors: Toshiaki Ueno, San Diego, CA (US); Alan R. Hargens, San Diego, CA (US); William T. Yost, Newport News, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 493 days.

(21) Appl. No.: 10/911,755

(22) Filed: Aug. 2, 2004

(65) Prior Publication Data

US 2006/0025686 A1    Feb. 2, 2006

(51) Int. Cl.
*A61B 8/00* (2006.01)
*A61B 8/12* (2006.01)
*A61B 8/14* (2006.01)

(52) U.S. Cl. .................. 600/443; 600/437; 600/438
(58) Field of Classification Search ................. 600/437, 600/438, 454, 455
See application file for complete search history.

(56) References Cited

U.S. PATENT DOCUMENTS

| | | | | |
|---|---|---|---|---|
| 3,885,551 A | * | 5/1975 | Massie | 600/495 |
| 4,363,242 A | * | 12/1982 | Heyman | 73/761 |
| 4,385,634 A | * | 5/1983 | Bowen | 600/407 |
| 4,711,248 A | * | 12/1987 | Steuer et al. | 600/561 |
| 4,735,211 A | * | 4/1988 | Takasugi | 600/443 |
| 4,794,933 A | * | 1/1989 | Yamazaki | 600/455 |
| 4,819,652 A | * | 4/1989 | Micco | 600/455 |
| 4,858,620 A | * | 8/1989 | Sugarman et al. | 600/587 |
| 4,984,567 A | * | 1/1991 | Kageyama et al. | 600/438 |
| 5,031,627 A | | 7/1991 | Yost et al. | |
| 5,150,620 A | | 9/1992 | Allison | |
| 5,214,955 A | | 6/1993 | Yost et al. | |
| 5,309,916 A | * | 5/1994 | Hatschek | 600/485 |
| 5,448,995 A | | 9/1995 | Yost et al. | |
| 5,564,435 A | * | 10/1996 | Steinberg | 600/561 |
| 5,617,873 A | * | 4/1997 | Yost et al. | 600/561 |
| 5,746,209 A | * | 5/1998 | Yost et al. | 600/453 |
| 5,841,032 A | | 11/1998 | Froggatt | |
| 6,007,489 A | | 12/1999 | Yost et al. | |
| 6,328,694 B1 | * | 12/2001 | Michaeli | 600/438 |
| 6,413,227 B1 | | 7/2002 | Yost et al. | |

(Continued)

OTHER PUBLICATIONS

Yost et al., "Constant Frequency Pulsed Phase-Locked-Loop Instrument for Measurement of Ultrasonic Velocity," (Rev. Sci. Instrum.) 62 (10), Oct. 1991.*

*Primary Examiner*—Brian L. Casler
*Assistant Examiner*—James Kish
(74) *Attorney, Agent, or Firm*—Helen M. Galus

(57) ABSTRACT

A method and apparatus for measuring pressure buildup in a body compartment that encases muscular tissue. The method includes assessing the body compartment configuration and identifying the effect of pulsatile components on at least one compartment dimension. This process is used in preventing tissue necrosis, and in decisions of whether to perform surgery on the body compartment for prevention of Compartment Syndrome. An apparatus is used for measuring excess pressure in the body compartment having components for imparting ultrasonic waves such as a transducer, placing the transducer to impart the ultrasonic waves, capturing the reflected imparted ultrasonic waves, and converting them to electrical signals, a pulsed phase-locked loop device for assessing a body compartment configuration and producing an output signal, and means for mathematically manipulating the output signal to thereby categorize pressure build-up in the body compartment from the mathematical manipulations.

39 Claims, 5 Drawing Sheets

U.S. PATENT DOCUMENTS

| | | |
|---|---|---|
| 6,475,147 B1 | 11/2002 | Yost et al. |
| 6,526,309 B1 | 2/2003 | Chance |
| 6,740,048 B2 | 5/2004 | Yost et al. |
| 6,746,410 B2 | 6/2004 | Yost et al. |
| 6,761,695 B2 | 7/2004 | Yost et al. |
| 6,773,407 B2 | 8/2004 | Yost et al. |
| 6,942,633 B2* | 9/2005 | Odland ............... 604/5.01 |
| 6,942,634 B2* | 9/2005 | Odland ............... 604/6.09 |
| 2002/0095087 A1 | 7/2002 | Mourad et al. |
| 2003/0109772 A1* | 6/2003 | Mills ................... 600/310 |
| 2005/0215898 A1* | 9/2005 | Yost et al. ........... 600/438 |
| 2005/0283092 A1* | 12/2005 | Gedebou ............. 600/561 |

* cited by examiner

METHOD AND APPARATUS TO ASSESS COMPARTMENT SYNDROME

ORIGIN OF THE INVENTION

The invention described herein was made in part by employees of the United States Government and may be manufactured and used by and for the Government of the United States for governmental purposes without the payment of any royalties thereon or therefore.

CROSS REFERENCE TO RELATED APPLICATION

This application is related to co-pending U.S. application Ser. No. 10/805,816 filed Mar. 22, 2004, entitled "Ultrasonic Apparatus and Method to Assess Compartment Syndrome."

FIELD OF THE INVENTION

The present invention provides novel processes, and apparatus for performing the processes, for interrogating a body compartment for compartment syndrome.

BACKGROUND OF THE INVENTION

Compartment Syndrome, which may cause Volkmann's Ischemic Contracture, occurs when bleeding and/or swelling interfere with proper blood circulation in enclosed groups of muscles and nerves. In the body, certain muscle groups, along with their indwelling blood vessels and nerve tissue, are covered by fascia, a noncompliant collagenous membrane, forming what is termed a "compartment." With bleeding and/or swelling, compartment pressure (CP) within the compartment increases, causing a decrease in venous, capillary, and ultimately, arterial blood flows. The network of blood vessels in the compartment becomes compressed by the pressure differential between the CP (exterior to the blood vessel) and the blood vessel interior; this impedes the rate of blood flow volume (RBFV) through the blood vessel network. Swelling occurs within the tissue, further restricting the blood flow. Although, according to the well-known Windkessel Theory, an occasional fluctuation in blood pressure pushes a bolus of blood through the blood vessel network, this normally is insufficient to reverse the continual deterioration of the muscle mass or maintain tissue viability. As the RBFV decreases over sufficient time and as CP rises, muscle viability deteriorates, with both nerve and muscle cells eventually dying from the lack of nutrients. Compartment Syndrome creates clinical signs such as acute pain and a progressive loss of muscle and nerve functions, usually in lower leg and forearm compartments, or possibly other body areas such as the wrist, buttocks, thigh, and upper arm. Potentially, any muscle of the body can experience a compartment syndrome. As pressures build over time and blood flow remains at abnormally low levels, myoneural necrosis occurs, leading to permanent injury (Volkmann's Contracture) and possible amputation of the limb.

Compartment Syndrome most commonly occurs with trauma or substantial injury to the body, such as a broken or crushed arm or leg (frequently resulting in Acute Compartment Syndrome), with some occurrences of Compartment Syndrome coming from tight bandages or surgery (which can result in Acute Compartment Syndrome) or extended exercise (Chronic [exertional] Compartment Syndrome). After trauma to a given area, a person may experience pain or an inability to use the muscles in the injured area. Surgery, such as cutting the fascia, can be performed to decrease the compartment pressure and increase blood flow to the muscle. As the fascia is substantially inelastic, swelling increases pressure within the body compartment, and muscles, blood vessels, and nerves within the compartment are compressed.

Even experienced physicians can have trouble making a reliable diagnosis of Compartment Syndrome. Known testing for Compartment Syndrome may include pressure measurement in the compartment by inserting a needle attached to a pressure meter. Compartment pressure of greater than 30-45 mmHg or pressures within 30 mmHg of the diastolic blood pressure indicate the presence of Compartment Syndrome if sufficient time has taken place.

U.S. Pat. No. 5,746,209 to Yost et al., entitled "Method of and Apparatus for Histological Human Tissue Characterization Using Ultrasound" discloses the use of ultrasound for determining histological characteristics of tissue by converting the return of energy pulses into numerical terms, useful in a diagnosis for the development of pressure ulcers. However, Yost et al. '209 does not address the diagnosis of Compartment Syndrome.

There is a need in the art to provide non-invasive determinations of CP associated with Compartment Syndrome. The present invention addresses this and other needs.

BRIEF SUMMARY OF THE INVENTION

The present invention includes a process for measuring CP buildup in one or more body compartments that encase muscular tissue comprising the steps of assessing a body compartment configuration and utilizing pulsatile components (from the blood flow) to ascertain the dimensions/geometry of the body compartment; and the present invention also includes a method for preventing myoneural necrosis and an incision, as well as a non-incision product result from this process.

The present invention also includes an apparatus for assessing CP build-up in one or more body compartments that encase muscular tissue. This apparatus, depending upon the inventive embodiment being utilized, comprises one or more of the following: (a) a transmitting device (such as a transducer) for imparting ultrasonic waves into the one or more body compartments, (b) means for positioning the transmitting device adjacent to the one or more body compartments effective for imparting ultrasonic waves therein, (c) a receiver (which may, or may not, be part of the transmitting device) for capturing a series of reflections of the imparted ultrasonic waves from the interior of the tissue bounded by the compartment fascia, and converting these reflected waves into data, such as electrical signals, (d) a pulsed phase locked loop to receive and utilize one or more signals corresponding to reflections from the fascia enclosing the compartment, (e) means for mathematically manipulating the output derived from a phase comparison within a pulsed phase locked loop, and (f) means for categorizing intramuscular pressure in the one or more body compartments from the mathematical manipulations.

In at least one embodiment, the present invention correlates dimensional changes in the body compartment to pulsatile blood pressure changes to ascertain whether blood flow is adequate to assure tissue viability. In at least one embodiment, the present invention relates the harmonic content contained within the response of the fascia walls to the intra-muscular pulsatile related or externally manipulated pressure fluctuations.

DETAILED DESCRIPTION OF THE INVENTION

The present invention provides a novel process and apparatus for interrogating a body compartment for Compartment Syndrome. Muscle groups in the arms, legs, and other body regions are encased in these body compartments that generally are tightly enclosed by fascia as well as bone. At maximum distension the membrane loses compliance to the point that excessive CP can build up within the tissues confined by the membrane. A pathological condition, Compartment Syndrome, can develop because of such excess CP build-up. Body compartments also possess extensive networks of blood vessels, known as blood vessel networks (BVN), which typically obscure non-invasive methods of analysis due to the fascial enclosures. The present invention affords a method and means to ascertain the build-up of excessive pressures in compartments which encase muscle and muscle groups thereby warning medical practitioners of the existence of potentially dangerous medical conditions, which when allowed to persist, generally result in tissue necrosis.

Figure 1:
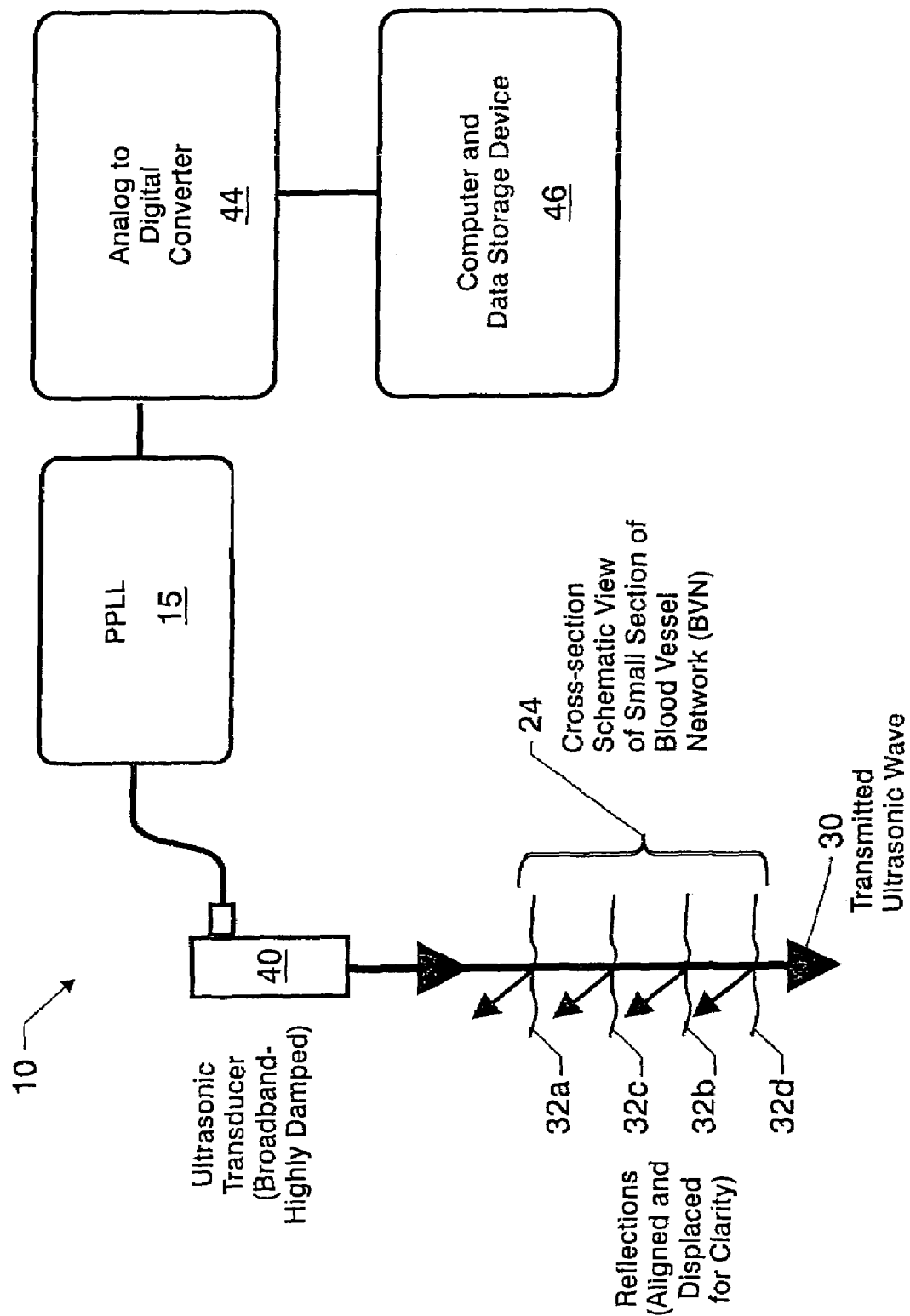
FIG. 1 is a schematic representation of an apparatus of the present invention.

The process of the present invention measures CP buildup in one or more osseofascial compartments that encase muscular tissue by assessing a body compartment configuration, identifying the effect of the pulsatile components on the dimensions of the body compartment, to determine the presence or absence of Compartment Syndrome. As seen in FIGS. 1 and/or 2, the present invention includes an apparatus 10 for measuring pressure build-up in one or more body compartments 20 that encase muscular tissue. Referring to the schematic of FIG. 1, a representative equipment arrangement of the apparatus 10 in operation is shown. As shown, the apparatus 10 of the present invention includes a transducer 40 as a means for imparting ultrasonic waves 30 through the skin 22 (shown in FIG. 2), overlaying the body compartment 20. The transducer 40 includes a device by which energy can flow from one or more transmission systems to one or more other transmission systems. Transducer imparting devices 40 of the present invention may include a variety of known devices, for example, a broadband ultrasonic transmit/receiver transducer.

In operation, as shown, the transducer 40 is energized with an electrical tone burst (from the pulsed phase-locked loop device 15) which generates the ultrasonic pulse (UP) incorporating the ultrasonic wave 30. The UP 30 travels through the skin 22 and into the underlying tissues in the region of the compartment 20 as well as through the compartment 20, into the tissues contained by the compartment 20. Reflections 32 occur at each impedance discontinuity 32a, 32b, 32c, 32d, or each tissue interface, and are received at the transducer 40 in the sequence which they occur. The transducer 40 converts the ultrasonic sequence received back from the segment into an electrical sequence which can be amplified and sent to pulsed phase-locked loop device 15.

Referring again to FIG. 2, the transducer 40 is positionally located in a manner for effectively interrogating a body compartment 20 for Compartment Syndrome characterization thereof. Placement of the transducer 40 positions the release (imparting) of ultrasonic waves 30 into the body compartment 20 for obtaining relevant data related to the body compartment 20 from one or more reflections 32 of the imparted ultrasonic waves 30 (FIG. 1). The means for effectively positioning the transducer 40 to obtain data from the at least one reflections 32 of the imparted ultrasonic waves 30 allows capture of the reflected ultrasonic wave(s) 32 from the body compartment 20, and retention and manipulation of data contained therein. One method of positioning the transducer 40 relative to the body compartment 20 includes placing the ultrasonic transducer 40 against the skin 22 of the extremity using a gel medium 48 for attaching the ultrasonic transducer 40 to the skin 22 adjacent to the body compartment 20. The gel medium 48 may serve as a couplant, and if needed, may be used to make a delay line for the ultrasonic wave transmission. Gel mediums 48 may include viscous substances that temporarily adhere the transducer 40 to the skin 22, such as those commonly known as ultrasound coupling gels. Additionally, for mechanical stability the transducer 40 may be inserted into the center of a disk 50, which can be taped, or otherwise secured, to a patient.

Figure 2:
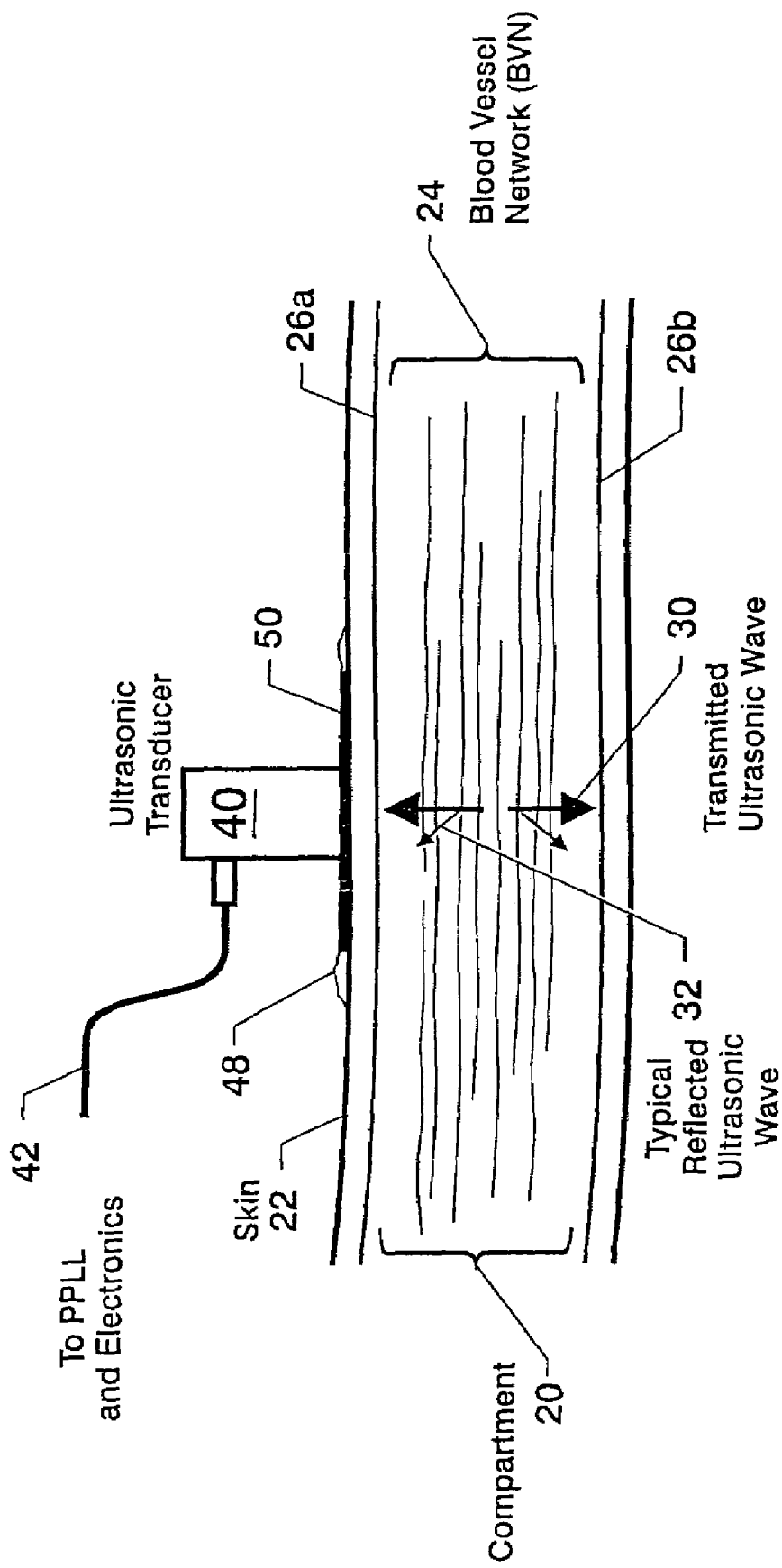
FIG. 2 is a schematic representation of ultrasonic interrogation of a body compartment of the present invention.

As seen in FIGS. 1 and 2, with the placement of the transducer 40 on the skin 22, and the generation of ultrasonic waves 30 into the body compartment 20, the imparted ultrasonic waves 30 are reflected (32) as they impinge on different surface layers within, and outside of, the body compartment 20, such as the compartment boundaries 26, identified as upper boundary 26a and lower boundary 26b, or BVN 24. The body compartment 20 may be placed at maximum distension prior to assessing the body compartment 20 configuration. As shown, the ultrasonic transducer 40 is further connected to a pulsed phase-locked loop device 15 and an appropriate electronics package 44/46, for fully utilizing the ultrasonic transducer 40 to investigate for Compartment Syndrome.

Referring again to FIG. 1, these reflected waves 32 can be captured for analysis (one at a time) by the pulsed phased-locked loop device 15, as described below. The pulsed phase-locked loop signal can be converted from an analog to a digital signal by an analog to digital converter 44 (which in at least one embodiment can be part of the retention means 46). Additionally, any appropriate retention means 46, generally suited to a specific medical purpose, can be employed. Representative retention means 46 can include, for example without limitation, data storage, data display, data transmission, data analysis, and/or combinations thereof. For example, emergency triage teams may use data display and/or data transmission means to address urgent medical needs. Therapeutic centers may primarily use data comparisons for monitoring treatments. Data storage is preferably used in most medical situations for training, medical review, and/or trend analysis. Computer manipulations, storage, and other data methodologies using computer and data storage devices 46, or other like devices, may include data prior to, during, and/or after mathematical manipulations, detailed below, are performed on the captured data. In at least one embodiment, the electronics package 44/46 includes a digital oscilloscope with fast Fourier Transform capability detailed below.

Mathematical manipulations include organization and processing of the data in any appropriate manner that defines one or more of these layers, as desired. In at least one embodiment the mathematical manipulation of the pulsed phase-locked loop signal includes Fourier Transform manipulation. The Fourier Transform manipulations of the data allow categorization of pressure build-up in the interrogated body compartment. As Compartment Syndrome is most prevalent in arms and/or legs, these body masses are typically investigated, although other body compartments 20 also may be interrogated for pressure buildup. Aspects of tissue characterization are described in U.S. Pat. No. 5,746,209 to Yost et al., entitled "Method of and Apparatus for Histological Human Tissue Characterization Using Ultrasound," the disclosure of which is hereby incorporated by reference as if set forth in its entirety herein.

With the transducer 40 positioned on, and transmitting ultrasonic waves 30 into the skin 22, body compartments 20 are interrogated with the capture of the reflected ultrasonic waves 32. The apparatus 10 of the present invention can include identifying a ratio of high frequency amplitudes to low frequency amplitudes present in the mathematical manipulation of the data derived from the captured ultrasonic waves for categorization of the CP build-up.

Figure 3:
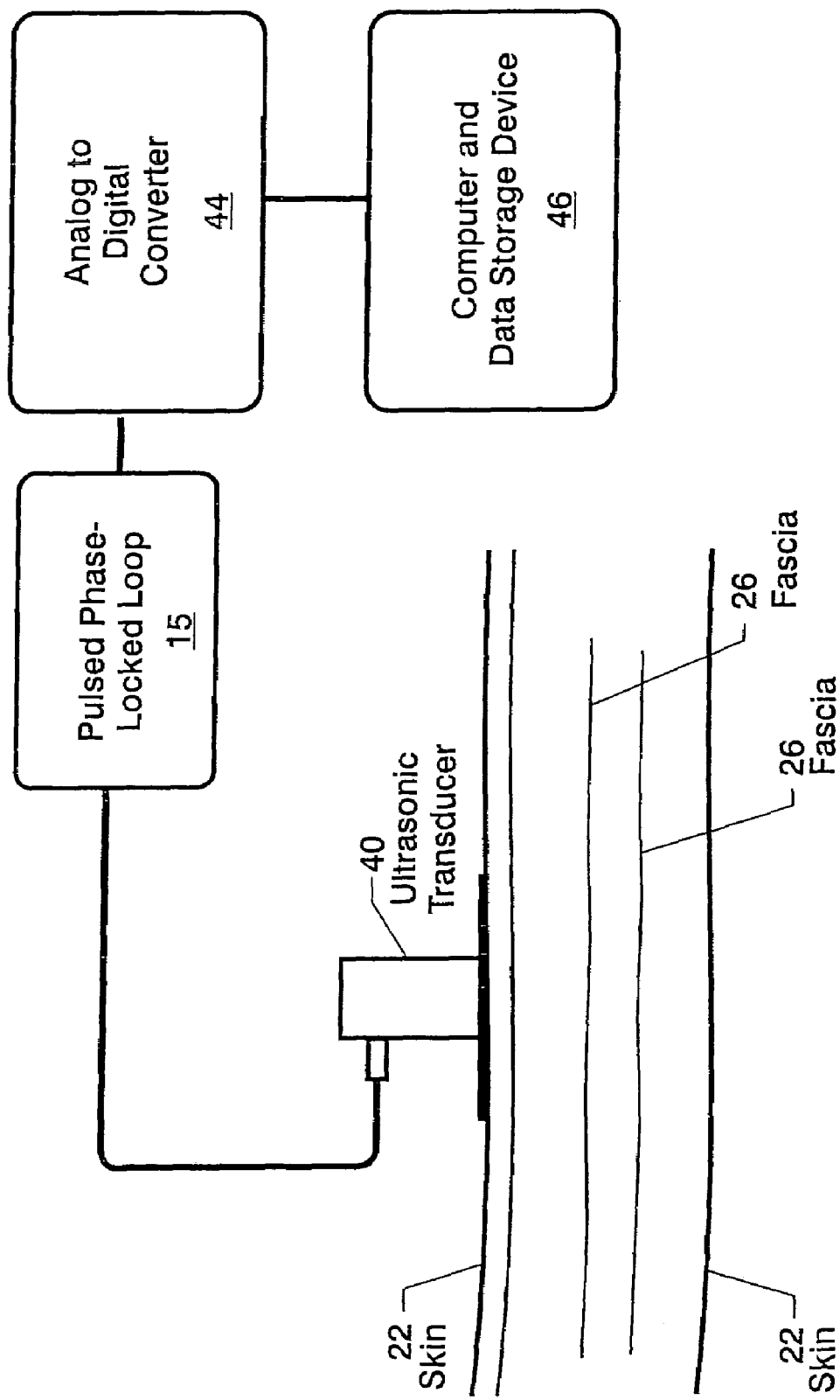
FIG. 3 is a schematic representation of the fascia dynamics technique used in the present invention.

In one embodiment, operation of the Fourier Transform manipulations of the fascia response provides necessary information of the ratio of high frequency amplitudes to low frequency amplitudes to identify onset, presence, or absence of Compartment Syndrome. An analysis based on this ratio can show a change in fascia response indicating a change in pressure within the compartment. A schematic outline of equipment in accordance with this embodiment, including pulsed phase-locked loop 15, is shown in FIG. 3.

Devices and techniques for providing and analyzing ultrasound with a pulsed phase-locked loop (both variable and constant frequency) can be found in U.S. Pat. No. 5,214,955 to Yost et al., entitled "Constant Frequency Pulsed Phase-Locked Loop Measuring Device," and U.S. Pat. No. 6,475,147, to Yost et al., entitled "Ultrasonic Apparatus and Technique to Measure Changes in Intracranial Pressure," (which addresses the use of ultrasound with a pulsed phase-locked loop for use with measurement of changes in intracranial pressure by monitoring the skull expansion caused by excessive pressure with the cranial cavity, yet does not address the application to the diagnosis of Compartment Syndrome) which patents are hereby incorporated herein by reference as if set forth in their entirety. Additionally, other known means for determining the pulsatile component can be utilized. For example, in at least one possible embodiment of the present invention other known phase shifting capabilities of pulsed phase-locked loops can be utilized to monitor the variation in the pulsatile components, such as those explained in the article by Yost, et al., *Fundamental Aspects of Pulse Phase-locked Loop Technology-based Methods for Measurement of Ultrasonic Velocity*, J. Acoust. Soc. Am. 91, 1456-1468 (1992), which article is hereby incorporated by reference as if set forth in its entirety herein.

Figure 4:
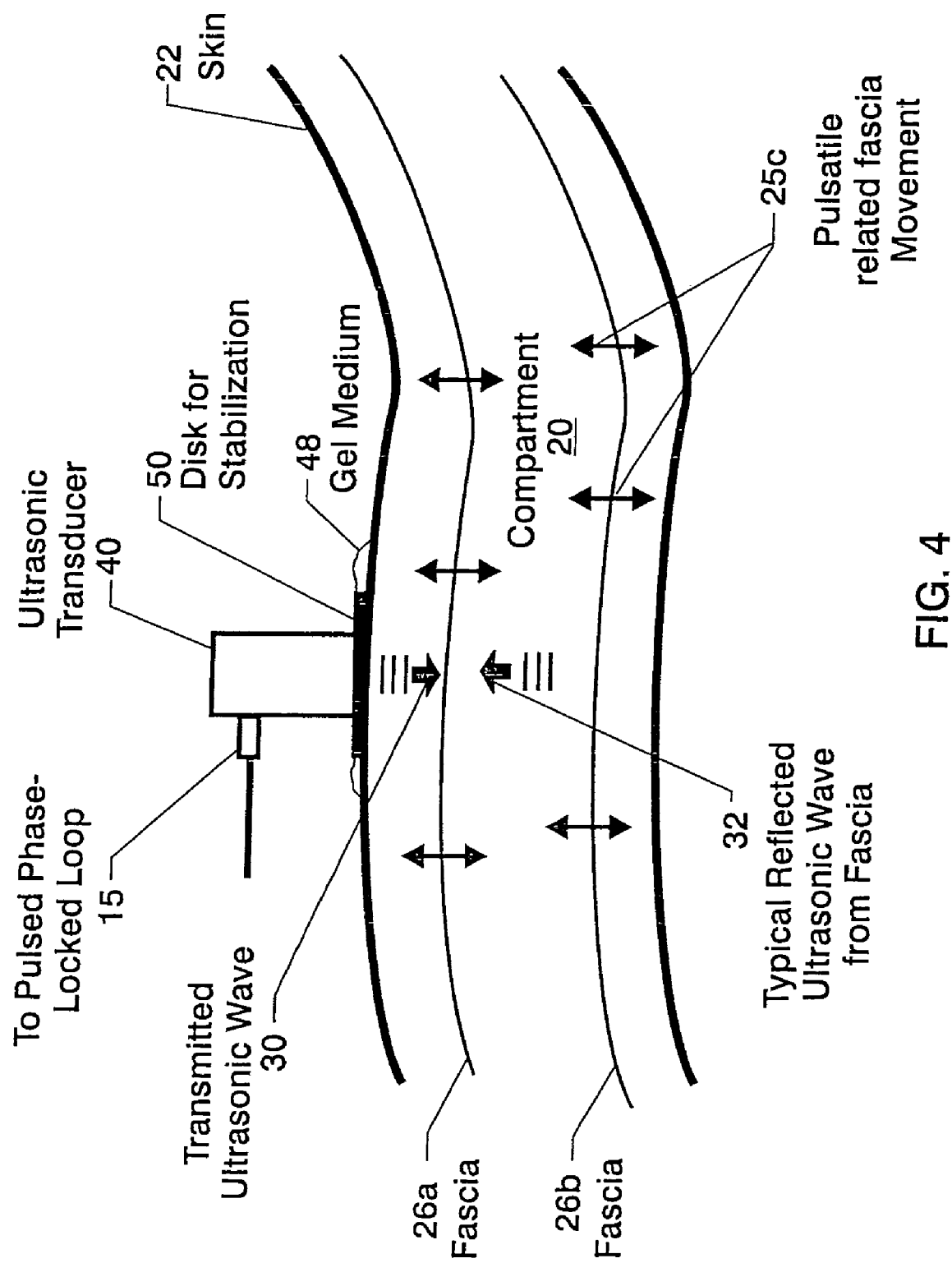
FIG. 4 is a schematic representation of use of pulsed phase-locked loop for measuring fascia dynamics.
Figure 5:
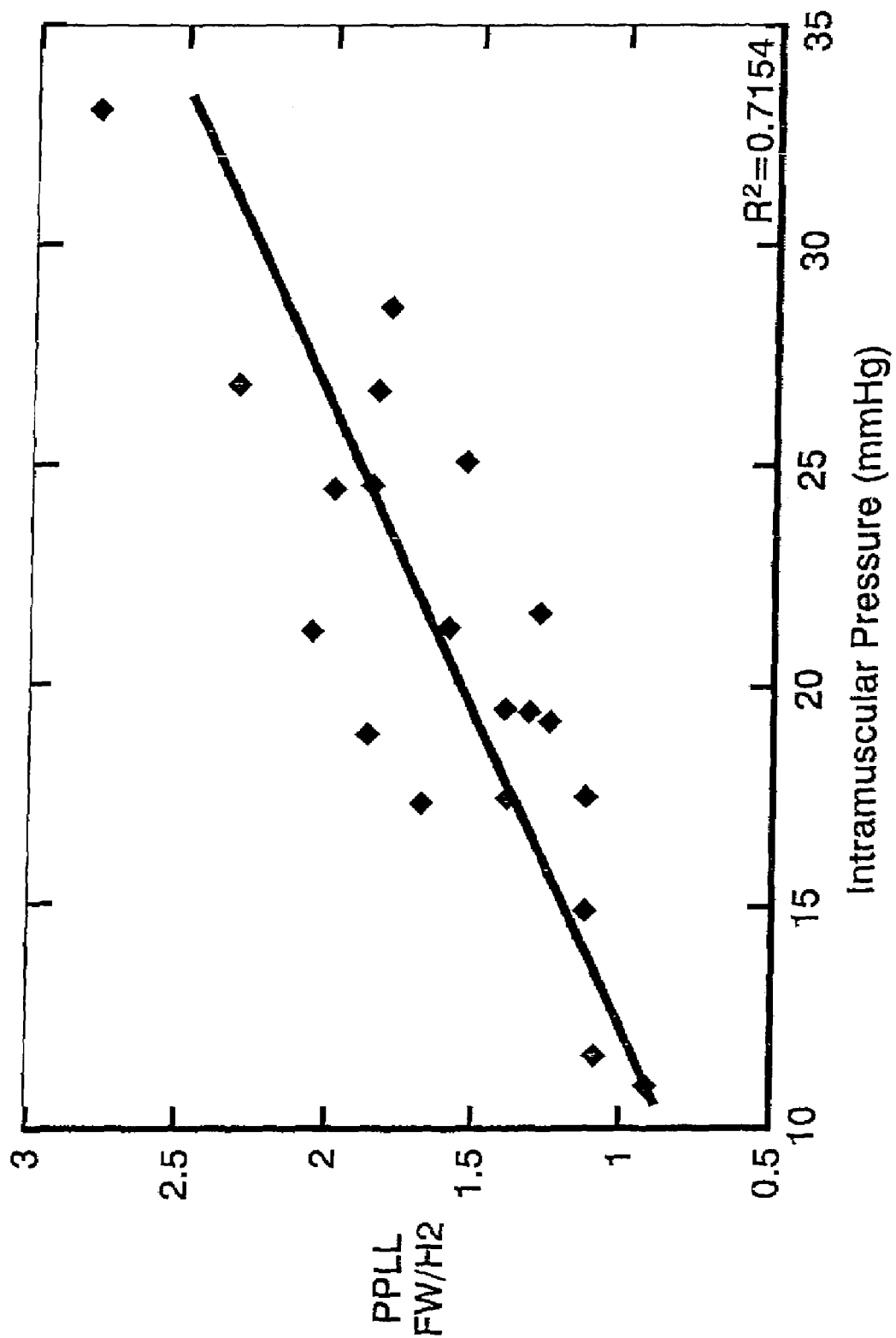
FIG. 5 is a graphic comparison between resultant data using pulsed phase-locked loop technique and directly measured intramuscular pressure.

As seen in FIG. 4, the essentially elongated body compartment 20 or osseofascial enclosure, having an upper 26a and lower 26b boundary, contains a muscle (not shown) midway in the compartment 20 that has sustained damage. The lower boundary 26b (opposite casing side from the ultrasonic transducer), which is substantially perpendicular to the propagation direction of the ultrasonic beam wave 30, constitutes the "lower edge," allowing the reflection boundary (and hence shape/configuration) to be monitored. In at least one embodiment, the pulsed phase-locked loop 15 responds accordingly by creating an output voltage which is in step with the movement of the fascia surface, i.e., a phase shifter compares the received ultrasonic signal (32) to a reference signal and develops a voltage ("error voltage") whenever their phase difference is a value other than 90° or 270°, to cause the received ultrasonic wave 32 signal (the ultrasonic reflection from the casing side opposite the insertion of the ultrasonic signal) to be at quadrature with the reference signal. A summing amplifier inside the pulsed phase-locked loop integrates the error voltage to become a control voltage to force the pulsed phase-locked loop to adjust the phase between the reference and the received ultrasonic signal to achieve quadrature. This control voltage is the "output" voltage from the pulsed phase-locked loop. As the fascia moves in response to the pulsatile intra-muscular pressure changes one monitors the output voltage which is in step with the pulsating boundary 26 of the compartment 20. In a normal body compartment 20 structure, the blood pulsations expand the compartment 20, which slightly moves the boundary 26 in step with the heartbeat. In an area of Compartment Syndrome, the compartment 20 has expanded to the point that the fascia is tight, and is unable to continue in a linear response with the expansion caused by blood pulsations. As such, the internal pressure in the compartment 20 compromises the ability to push the blood through the compartment 20. With the fascia becoming more nearly rigid, the pulsating of the fascial casing changes its character. Hence, the corresponding variations in the output voltage from the pulsed phase-locked loop changes wave form shape when referenced to the blood pressure wave form. Therefore, Fourier analysis of the output voltage of the pulsed phase-locked loop shows an increase in harmonic content relative to a compartment with low intra-muscular pressure. As shown in FIG. 5, the indication of increased harmonic ratio allows a clinician to determine the presence or absence of Compartment Syndrome.

The data shown in FIG. 5 were taken on a human volunteer, and compares intramuscular pressure (IMP) variations with pulsed phase-locked loop output variations during a manipulation to alter intra-muscular pressure in an anterior compartment, using a thigh cuff pressure bladder with a pressuring system commonly used with blood pressure measuring apparatus. Raw data was low-pass filtered at 5 Hz for harmonic analysis. As can be seen by the graph, a close correlation exists between the graph lines depicting: Invasive IMP measurement (Anterior compartment IMP); and the ratio of pulsed phase-locked loop waveform Harmonics 1 and 2 (PPLL FW/H2).

Using the inventive processes for monitoring the CP buildup, prevention of myoneural necrosis is possible. With the determination of the presence of Compartment Syndrome, corrective or preventive actions may be performed, such as cutting (slitting) the fascia to relieve the excessive CP. Conversely, when the absence of compartment syndrome is determined, detrimental actions such as cutting an incision may be avoided. This non-incision determination prevents unnecessary medical treatment, further benefiting muscle function, return of blood to the heart from the muscle pump, and ultimately, the health of a patient.

The foregoing summary, description, and examples of the present invention are not intended to be limiting, but are only exemplary of the inventive features that are defined in the claims.

What is claimed as new and desired to be secured by Letters Patent of the United States is:

1. A process for determining the presence or absence of excess pressure in one or more body compartments that encase muscular tissue, comprising the steps of:

assessing a body compartment configuration utilizing a pulsed phase-locked loop device, comprising the steps of:

transmitting temporal pulsed ultrasonic signals to the body compartment; and capturing and processing the temporal pulsed ultrasonic signals reflected off of at least one surface layer of the body compartment; and...

analyzing an output signal from the pulsed phase loop device, comprising the steps of:
determining dimensional changes of the body compartment; and
correlating the dimensional changes to pulsatile blood pressure changes to ascertain the presence or absence of excess pressure in the body compartment, wherein decreased dimensional changes are indicative of increased compartment pressure.

2. The process of claim 1, wherein the step of assessing a body compartment configuration comprises means for activation, transmission, and reception of ultrasonic waves.

3. The process of claim 1, wherein the step of assessing a body compartment configuration comprises identifying characteristics of the body compartment selected from the group consisting of upper compartment boundary, lower compartment boundary, blood vessel network, and combinations thereof.

4. The process of claim 3, wherein the step of assessing a body compartment configuration comprises identifying compartment boundary characteristics of the body compartment through a broadband ultrasonic transmit/receive transducer.

5. The process of claim 1, further comprising the step of placing the body compartment at maximum distension prior to assessing the body compartment configuration.

6. The process of claim 1, wherein the body compartment comprises an osseofascial enclosure group consisting of arm, leg, other muscle groups, and combinations thereof.

7. The process of claim 1, wherein the step of analyzing an output signal from the-pulsed phase-locked loop device comprises examining the pulsatile components of the output signal.

8. The process of claim 7, wherein the step of analyzing an output signal from the pulsed phase-locked loop device comprises the step of identifying a ratio of high-frequency amplitudes to low-frequency amplitudes present in mathematical manipulations of the output signal.

9. The process of claim 1, wherein the stop of assessing a body compartment configuration comprises the step of monitoring changes in a lower reflection boundary of the compartment.

10. The process of claim 9, wherein the step of monitoring changes in a lower reflection boundary of the compartment comprises the steps of:
capturing a wave reflected off of a lower compartment boundary; and
creating an output signal from the pulsed phase-locked loop device which is in step with the movement of the lower reflection boundary in response to pulsatile blood pressure changes.

11. The process of claim 1, wherein the step of correlating the dimensional changes comprises the step of analyzing variations in the output signal wave form shape when referenced to a blood pressure wave form.

12. The process of claim 1, wherein the step of analyzing an output signal from the pulsed phase-locked loop device comprises the step of performing a Fourier analysis of the output signal to determine if there is a change in the ratio of harmonic content which is indicative of Compartment Syndrome.

13. The process of claim 1 further comprising the step of alleviating at least a portion of the pressure build-up through the use of an incision product.

14. An apparatus for determining the presence or absence of excess pressure in one or more body compartments that encases muscular tissue, comprising a:
transmitting and receiving device comprising means for imparting ultrasonic waves into one or more body compartments and means for capturing the reflections of the imparted ultrasonic waves and converting them into electrical signals;
means for positioning the transmitting and receiving device adjacent to the one or more body compartments effective for imparting ultrasonic waves therein;
means for assessing the body compartment configuration of the one or more body compartments utilizing a pulsed phase-locked loop device; and
means for analyzing variations in an output signal from the pulsed phase-locked loop device, said analyzing means comprising:
means for determining dimensional changes of the body compartment; and
means for correlating the dimensional changes to pulsatile blood pressure changes to ascertain the presence or absence of excess pressure in the one or more body compartments.

15. The apparatus of claim 14, wherein the means for capturing and converting comprises a transducer.

16. The apparatus of claim 14, wherein the means for determining dimensional changes of the body compartment comprises means for examining the pulsatile components of the output signal.

17. The apparatus of claim 14, wherein the means for analyzing variations in the output signal comprises a means for:
mathematically manipulating the output signal; and
wherein the means for correlating the dimensional changes to pulsatile blood pressure changes comprises means for categorizing pressure in the one or more body compartments from the mathematical manipulations, and wherein decreased dimensional changes are indicative of increased compartment pressure.

18. The apparatus of claim 17, wherein the means for mathematical manipulation of the output signals comprises Fourier Transform manipulation.

19. The apparatus of claim 17, wherein the means for categorizing pressure further comprises means for analyzing harmonic content, to permit comparison with a compartment with low intra-muscular pressure.

20. The apparatus of claim 17, wherein the means for categorizing pressure in one or more body compartment comprises means for categorizing pressure in a body compartment selected from the group consisting of arms, legs, other muscle groups, and combinations thereof.

21. The apparatus of claim 14, wherein the means for positioning the transducer comprises at least one of a gel and a disc.

22. The apparatus of claim 14, wherein the means for analyzing variations in the output signals comprises a retention means selected from the group consisting of storage, display, analysis, and combinations thereof.

23. The apparatus of claim 14, wherein the means for determining dimensional changes of the body compartment comprises measuring changes in pulsatile components of at least one dimension of the body compartment.

24. An apparatus for determining excess pressure in one or more body compartments that encases muscular tissue, comprising:
- means for assessing a body compartment configuration comprising a means for transmitting and recieving ultrasonic signals and a pulsed phase-locked loop device; and, . . .
- means for analyzing an output signal from the pulsed phase-locked loop device to determine movement of a compartment boundary layer; and
- means for correlating the movement of the compartment boundary layer to pulsatile blood pressure changes to ascertain the presence or absence of excess pressure in the body compartment.

25. The apparatus of claim 24, wherein the means for transmitting and receiving ultrasonic signals comprises means for activation, transmission, and reception of ultrasonic waves.

26. The apparatus of claim 24, wherein the means for assessing a body compartment configuration comprises means for identifying characteristics of the body compartment selected from the group consisting of upper compartment boundary, lower compartment boundary, blood vessel network, and combinations thereof.

27. The apparatus of claim 26, wherein the means for transmitting and receiving ultrasonic signals comprises means for identifying compartment boundary characteristics of the body compartment through a broadband ultrasonic transmit/receive transducer.

28. The apparatus of claim 24, wherein the means for analyzing an output signal from the pulsed phase-locked loop device includes means for capturing temporal pulsed phase-locked loop signals.

29. The apparatus of claim 28, wherein the means for capturing temporal pulsed plmtse-locked loop signals includes means for processing the temporal pulsed phase-locked loop signals.

30. The apparatus of claim 24, wherein the body compartment is placed at maximum distension prior to assessing the body compartment configuration.

31. The apparatus of claim 24, wherein the body compartment comprises a tubular shaped collagenous membrane selected from the group consisting of arm, leg, other muscle groups, and combinations thereof.

32. The apparatus of claim 24, wherein the means for analyzing an output signal from the pulsed phase-locked loop device comprises means for examining the pulsatile components of the output signal.

33. The apparatus of claim 32, wherein the means for examining the pulsatile components of the output signal comprises means for identifying a ratio of high-frequency amplitudes to low-frequency amplitudes present in mathematical manipulations of the output signal.

34. The apparatus of claim 24, wherein the means for assessing a body compartment configuration comprises means for monitoring changes in a lower reflection boundary of the compartment.

35. The apparatus of claim 34, wherein the means for monitoring changes in a lower reflection boundary of the compartment comprises:
- means for capturing a wave reflected off of the a lower compartment boundary; and
- means for creating an output signal from the pulsed phase-locked loop device which is in step with the movement of the lower reflection boundary in response to pulsatile pressure changes.

36. The apparatus of claim 24, wherein the means for correlating the movement of the compartment boundary layer to pulsatile pressure changes comprises means for analyzing variations in the output signal wave form shape when referenced to a blood pressure wave form, and wherein decreased boundary layer movement is indicative of increased compartment pressure.

37. The apparatus of claim 24, wherein the means for analyzing an output signal from the pulsed phase-locked loop device comprises means for performing a Fourier analysis of the output signal to determine if there is a change in the ratio of harmonic content which is indicative of Compartment Syndrome.

38. A method for producing an incision product produced by determining the presence of Compartment Syndrome comprising the step of utlizing the apparatus of claim 24 to determine the presence of Compartment Syndrome.

39. An apparatus for categorizing pressure in one or more body compartments that encases muscular tissue, comprising:
- at least one transducer for imparting ultrasonic waves into the one or more body compartments, capturing reflections of the imparted waves, and converting them into electrical signals;
- means for positioning the at least one transducer adjacent to the one or more body compartments effective for imparting ultrasonic waves therein;
- a pulsed phase-locked loop device for utilizing the electrical signals to assess a body compartment configuration, and generate an output voltage;
- means for manipulating the output voltage of the pulsed phase-locked loop device so as to determine the movement of at least one boundary layer of the compartment; and,
- means for categorizing pressure in the one or more body compartments from the movement of the at least one boundary layer, wherein decreased boundary layer movement is indicative of increased compartment pressure.

* * * * *